(12) United States Patent
Shum et al.

(10) Patent No.: US 8,956,228 B2
(45) Date of Patent: Feb. 17, 2015

(54) GAME POD

(75) Inventors: Albert Shum, Portland, OR (US);
Charles Whipple Case, Jr., Lake Oswego, OR (US); Allan M. Schrock, Portland, OR (US)

(73) Assignee: Nike, Inc., Beaverton, OR (US)

( * ) Notice: Subject to any disclaimer, the term of this patent is extended or adjusted under 35 U.S.C. 154(b) by 1490 days.

(21) Appl. No.: 11/055,581

(22) Filed: Feb. 10, 2005

(65) Prior Publication Data

US 2005/0227811 A1    Oct. 13, 2005

Related U.S. Application Data

(63) Continuation-in-part of application No. 10/827,989, filed on Apr. 19, 2004, now abandoned, and a continuation-in-part of application No. 10/431,331, filed on May 6, 2003, which is a continuation of application No. 09/453,645, filed on Dec. 3, 1999, now Pat. No. 6,585,622.

(51) Int. Cl.
*A63F 13/00*    (2014.01)
*A43D 999/00*    (2006.01)
(Continued)

(52) U.S. Cl.
CPC ............ *A43D 999/00* (2013.01); *A43B 3/0005* (2013.01); *A63B 24/0021* (2013.01);
(Continued)

(58) Field of Classification Search
USPC ............. 463/36–37, 39, 1, 7; 36/132; 482/79; 73/172
See application file for complete search history.

(56) References Cited

U.S. PATENT DOCUMENTS 1,963,110 A    6/1934    Assael
3,797,010 A    3/1974    Adler et al.
(Continued)

FOREIGN PATENT DOCUMENTS

EP    0908701 A2    4/1999
JP    63186711    11/1988
(Continued)

OTHER PUBLICATIONS

International Search Report in corresponding PCT application, application No. PCT/US2005/012954, mailed Aug. 26, 2005.
(Continued)

*Primary Examiner* — Jasson Yoo
(74) *Attorney, Agent, or Firm* — Banner & Witcoff Ltd.

(57) ABSTRACT

A system for promoting physical activity for video game players. A video game player wears an article of footwear with a physical activity monitor or "game pod" mounted thereon while exercising or performing some other type of physical activity. The game pod measures the amount of the player's physical activity, and records that amount in a memory. When the player desires to play a video game according to the invention, the player disengages at least the memory from the article of footwear, and then engages the memory with the computer hosting the video game through a computer interface. The computer then obtains the recorded amount of physical activity, and provides a computer function associated with the recorded amount of physical activity. The computer function may include the initiation of the video game itself, the instantiation of a specified gaming environment within the video game, the instantiation of one or more specified characteristics for the player's avatar within the video game, a lengthened playing time for the user's avatar, allowing the player to access data associated with the video game, or a combination of two or more of these functions.

4 Claims, 10 Drawing Sheets

(51) Int. Cl.

| | |
|---|---|
| *A43B 3/00* | (2006.01) |
| *A63B 24/00* | (2006.01) |
| *A63B 71/06* | (2006.01) |
| *A63F 13/98* | (2014.01) |
| *G06F 19/00* | (2011.01) |
| *A61B 5/103* | (2006.01) |

(52) U.S. Cl.
CPC ......... *A63B24/0087* (2013.01); *A63B 71/0622* (2013.01); *A63F 13/02* (2013.01); *G06F 19/3481* (2013.01); *A61B 5/1036* (2013.01); *A63B 2024/0025* (2013.01); *A63B 2024/0096* (2013.01); *A63B 2208/12* (2013.01); *A63B 2220/12* (2013.01); *A63B 2220/40* (2013.01); *A63B 2225/20* (2013.01); *A63B 2225/50* (2013.01); *A63B 2230/00* (2013.01); *A63B 2230/06* (2013.01); *A63F 2300/1012* (2013.01); *A63F 2300/105* (2013.01); *A63F 2300/205* (2013.01); *A63F 2300/609* (2013.01); *A63F 2300/65* (2013.01)
USPC ................. 463/36; 463/1; 463/7; 473/49

(56) References Cited

U.S. PATENT DOCUMENTS

| | | | |
|---|---|---|---|
| 3,934,065 A | | 1/1976 | Tung |
| 4,104,102 A | | 8/1978 | Eagon et al. |
| 4,510,704 A | | 4/1985 | Johnson |
| 4,517,685 A | | 5/1985 | Lesley |
| 4,542,897 A | | 9/1985 | Melton et al. |
| 4,651,446 A | * | 3/1987 | Yukawa et al. ............... 36/132 |
| 4,716,458 A | | 12/1987 | Heitzman et al. |
| 4,743,971 A | | 5/1988 | Hugli |
| 4,752,764 A | | 6/1988 | Peterson et al. |
| 4,769,265 A | | 9/1988 | Coburn, Jr. |
| 4,771,394 A | | 9/1988 | Cavanagh |
| 4,808,471 A | | 2/1989 | Grunzinger |
| 4,828,257 A | | 5/1989 | Dyer et al. |
| 4,856,787 A | | 8/1989 | Itkis |
| 4,919,418 A | | 4/1990 | Miller |
| 4,925,189 A | | 5/1990 | Braeunig |
| 5,017,770 A | | 5/1991 | Sigalov |
| 5,089,960 A | | 2/1992 | Sweeney, Jr. |
| 5,203,848 A | | 4/1993 | Wang |
| 5,210,604 A | | 5/1993 | Carpenter |
| 5,213,555 A | | 5/1993 | Hood et al. |
| 5,235,416 A | | 8/1993 | Stanhope |
| 5,423,554 A | | 6/1995 | Davis |
| 5,456,648 A | | 10/1995 | Edinburg et al. |
| 5,466,200 A | | 11/1995 | Ulrich et al. |
| 5,524,637 A | * | 6/1996 | Erickson ................. 600/592 |
| 5,547,439 A | | 8/1996 | Rawls et al. |
| 5,575,717 A | | 11/1996 | Houriet, Jr. et al. |
| 5,594,469 A | | 1/1997 | Freeman et al. |
| 5,616,078 A | | 4/1997 | Oh et al. |
| 5,626,537 A | | 5/1997 | Danyo et al. |
| 5,655,997 A | | 8/1997 | Greenberg et al. |
| 5,675,828 A | | 10/1997 | Stoel et al. |
| 5,720,200 A | * | 2/1998 | Anderson et al. ............... 73/172 |
| 5,768,382 A | | 6/1998 | Schneier et al. |
| 5,785,632 A | | 7/1998 | Greenberg et al. |
| 5,794,267 A | | 8/1998 | Wallace |
| 5,864,333 A | * | 1/1999 | O'Heir .................. 345/157 |
| 5,890,995 A | | 4/1999 | Bobick et al. |
| 5,890,997 A | | 4/1999 | Roth |
| 5,899,963 A | * | 5/1999 | Hutchings .................. 702/145 |
| 5,916,063 A | | 6/1999 | Alessandri |
| 5,921,891 A | | 7/1999 | Browne |
| 5,941,797 A | | 8/1999 | Kashiwaguchi |
| 5,974,262 A | | 10/1999 | Fuller et al. |
| 5,982,352 A | | 11/1999 | Pryor |
| 5,989,157 A | | 11/1999 | Walton |
| 6,013,007 A | | 1/2000 | Root et al. |
| 6,018,705 A | * | 1/2000 | Gaudet et al. ............... 702/176 |
| 6,024,675 A | * | 2/2000 | Kashiwaguchi ................. 482/4 |
| 6,050,924 A | | 4/2000 | Shea |
| 6,066,075 A | | 5/2000 | Poulton |
| 6,077,193 A | | 6/2000 | Buhler et al. |
| 6,122,340 A | * | 9/2000 | Darley et al. ................ 377/24.2 |
| 6,122,960 A | | 9/2000 | Hutchings et al. |
| 6,175,960 B1 | | 1/2001 | Knittel |
| 6,191,773 B1 | | 2/2001 | Maruno et al. |
| 6,213,872 B1 | * | 4/2001 | Harada et al. .................. 463/7 |
| 6,222,859 B1 | | 4/2001 | Yoshikawa |
| 6,231,527 B1 | | 5/2001 | Sol |
| 6,298,218 B1 | | 10/2001 | Lowe et al. |
| 6,298,314 B1 | | 10/2001 | Blackadar et al. |
| 6,405,381 B1 | | 6/2002 | Bowman, Jr. |
| 6,475,115 B1 | * | 11/2002 | Candito et al. .................. 482/4 |
| 6,539,336 B1 | | 3/2003 | Vock et al. |
| 6,545,705 B1 | | 4/2003 | Sigel et al. |
| 6,572,511 B1 | | 6/2003 | Volpe |
| 6,585,622 B1 | | 7/2003 | Shum et al. |
| 6,595,858 B1 | * | 7/2003 | Tajiri et al. ................ 463/31 |
| 6,605,038 B1 | | 8/2003 | Teller et al. |
| 6,669,600 B2 | | 12/2003 | Warner |
| 7,106,360 B1 | | 9/2006 | Frederick |
| 2002/0019258 A1 | | 2/2002 | Kim et al. |
| 2002/0019296 A1 | | 2/2002 | Freeman et al. |
| 2002/0036617 A1 | | 3/2002 | Pryor |
| 2002/0077219 A1 | | 6/2002 | Cohen et al. |
| 2002/0083507 A1 | | 7/2002 | Mullis |
| 2002/0097247 A1 | | 7/2002 | Ohba |
| 2002/0160883 A1 | * | 10/2002 | Dugan .................. 482/8 |
| 2002/0176575 A1 | * | 11/2002 | Qawami et al. ............... 380/201 |
| 2003/0008714 A1 | | 1/2003 | Tajiri et al. |
| 2003/0016368 A1 | | 1/2003 | Aman et al. |
| 2003/0050537 A1 | | 3/2003 | Wessel |
| 2004/0017473 A1 | | 1/2004 | Marks |
| 2004/0127334 A1 | | 7/2004 | Heppert |
| 2004/0127336 A1 | | 7/2004 | Lapcevic |

FOREIGN PATENT DOCUMENTS

| | | |
|---|---|---|
| JP | 04-127674 B2 | 4/1992 |
| JP | 05-161724 | 6/1993 |
| JP | 07-185131 | 7/1995 |
| JP | 2000-033184 | 2/2000 |
| JP | 2001-155121 | 6/2001 |
| JP | 2002500768 | 1/2002 |
| JP | 2002519754 A | 7/2002 |
| JP | 2002-530970 | 9/2002 |
| JP | 2003221712 A | 8/2003 |
| JP | 2003316905 A | 11/2003 |
| JP | 2003333578 A | 11/2003 |
| JP | 2004264244 A | 9/2004 |
| JP | 2004-313407 | 11/2004 |
| WO | 9967702 A1 | 12/1999 |
| WO | 0031560 A2 | 6/2000 |
| WO | 0171397 A1 | 9/2001 |
| WO | 2005002436 | 1/2005 |

OTHER PUBLICATIONS

Office Action dated May 31, 2010 in Japanese Application No. 2007-555194 along with an English language translation.

Chinese Application No. 2005800199298, Chinese Language Version and English Language Translation of Decision of Rejection dated Jun. 2, 2011.

Chinese Application No. 200580019929.8, Chinese Language Version and English Language Translation of Notification of Reexamination dated May 28, 2013.

Office Action issued in U.S. Appl. No. 10/431,331 dated Oct. 10, 2013.

Printout of Web page (Netpulse Frequent Fitness Program), dated Dec. 3, 1999, 3 pgs.

Printout of Web page from Interactive Fitness Technologies, Inc. (UltraCoach Standard), dated Nov. 30, 1999, 3 pgs.

Printout of Web page from Interactive Fitness Technologies. Inc. (UltraCoach Multi-Sport Training Software Products Catalog), dated Sep. 1999, 12 pgs.

(56) References Cited

OTHER PUBLICATIONS

Printout of Web page from Interactive Fitness Technologies, Inc. (UltraCoach VR: How it Works?), dated Nov. 30, 1999, 2 pgs.
Printout of Web page from Interactive Fitness Technologies, Inc. (UltraCoach VR Features), dated Nov. 30, 1999, 3 pgs.
Printout of Web page from Interactive Fitness Technologies, Inc. (UltraCoach Fit Software Comparisons), dated Nov. 30, 1999, 2 pgs.
Printout of Web page from Interactive Fitness Technologies, Inc. (UltraCoach Home Page), dated Nov. 30, 1999, 2 pgs.
Health Care. High-Tech Style.' by Bernard Wyskockl, Jr:, The Well Street Journal, Apr. 17, 2001, 2 pgs.
Extended Search Report related in European Patent Application No. 09150346.6; dated Jan. 2, 2012.
Extended Search Report from European Patent Application No. 10178921.2; dated May 27, 2011.
Guskov, I., "Efficient Tracking of Regular Patterns on Non-rigid Geometry", University of Michigan, 2002: 1057-1060.
Extended Search Report from related European Patent Application No. 10150066.8; dated May 31, 2011.
European Search Report in related European Application No. 10179570.6; dated Jul. 24, 2012.

\* cited by examiner

GAME POD

This application claims priority to U.S. patent application Ser. No. 10/827,989, entitled "Sigils For Use With Apparel" and naming Albert Shum et al. as inventors, filed Apr. 19, 2004, which application is incorporated entirely herein by reference. This application also claims priority to U.S. patent application Ser. No. 10/431,331, entitled "Interactive Use And Athletic Performance Monitoring And Reward Method, System And Computer Program Product" and naming Albert Shum et al. as inventors, filed May 6, 2003, which in turn was a continuation application of U.S. patent application Ser. No. 09/453,645, entitled "Interactive Use And Athletic Performance Monitoring And Reward Method, System And Computer Program Product" and naming Albert Shum et al. as inventors, filed Dec. 3, 1999, which application issued on Jul. 1, 2003 as U.S. Pat. No. 6,585,622, which applications also are incorporated entirely herein by reference.

FIELD OF THE INVENTION

The present invention relates to a physical activity monitor, positioned on an article of footwear, that interfaces with a computing device. The present invention also relates to computing devices that provide a user with functionality based upon an amount of physical activity recorded by a physical activity device. Various aspects of the present invention are particularly applicable to a system that employs a physical activity monitor mounted on an article of footwear to record a user's physical activity and a computer game that provides the user with rewards in a gaming environment based upon the recorded amount of physical activity.

BACKGROUND OF THE INVENTION

Graphics-based computer games, typically referred to as "video" games, have evolved significantly in the last three decades. Early video games provided only basic monochromatic images and required only simple playing strategies. Conventional video games, however, employ dazzling three-dimensional color images, and many offer elaborate storylines with sophisticated playing strategies. As a result, the popularity of video games has increased dramatically in the last few years. Some age groups even play video games more often on average than they watch television or participate in other forms of entertainment.

One reoccurring criticism of conventional video games, however, is that their sophistication lures frequent players into a sedentary lifestyle. This criticism is particularly disconcerting with regard to younger children, for whom exercise and other physical activity is important for their future health. Some video game manufacturers have attempted to address this problem by providing interactive games. These games require some physical activity from the player to control the operation of the game. The amount of physical activity permitted by these interactive video games, however, is limited. For example, these interactive video games typically oblige the player to remain on a pressure sensitive pad or in front of a camera. Accordingly, it would be beneficial to develop video games that encourage significant physical activity from players, rather than discouraging physical activity.

BRIEF SUMMARY OF THE INVENTION

Advantageously, various examples of the invention promote physical activity for video game players. According to some examples of the invention, a video game player wears an article of footwear with a physical activity monitor or "game pod" mounted thereon while exercising or performing some other type of physical activity. The game pod measures the amount of the player's physical activity, and records that amount in a memory. When the player desires to play a video game according to the invention, the player disengages at least the memory from the article of footwear, and then engages the memory with the computer hosting the video game through a computer interface. The computer then obtains the recorded amount of physical activity, and provides a computer function associated with the recorded amount of physical activity. The computer function may be, for example, the initiation of the video game itself, the instantiation of a specified gaming environment within the video game, the instantiation of one or more specified characteristics for the player's avatar within the video game, a lengthened playing time for the user's avatar, allowing the player to access data associated with the video game, or a combination of two or more of these functions.

A game pod according to various examples of the invention may include a physical activity detector that measures an amount of the user's physical activity and a memory that stores the amount of physical activity measured by the physical activity detector. The game pod may also include a computer interface that allows the memory to interface with a computer hosting a video game according to various examples of the invention. With some implementations of the invention, the game pod may also have a display. The display may, for example, provide an indication of the amount of physical activity recorded in the memory. Some implementations of the game pod may alternately or additionally have a transfer switch that initiates the transfer of the recorded amount of physical activity from the memory to the computer. Still further, with some embodiments of the invention, one or more components of the game pod may be integrally formed with or incorporated into an article of foot wear. Other embodiments of the invention may alternately include a mount for removably mounting the game pod on an article of footwear.

A video game according to various examples of the invention will include a game module for executing the operations of a video game. It also may include a supplemental functionality module that provides one or more additional functions to the video game based upon the amount of physical activity recorded in the memory of the player's game pod. Further, the video game may include a functionality determination module that determines which of the additional functions the video game will provide. The functionality determination module will select one or more functions that correspond to the amount of physical activity stored in the game pod memory.

DETAILED DESCRIPTION OF THE INVENTION

Example Computer

Figure 1:
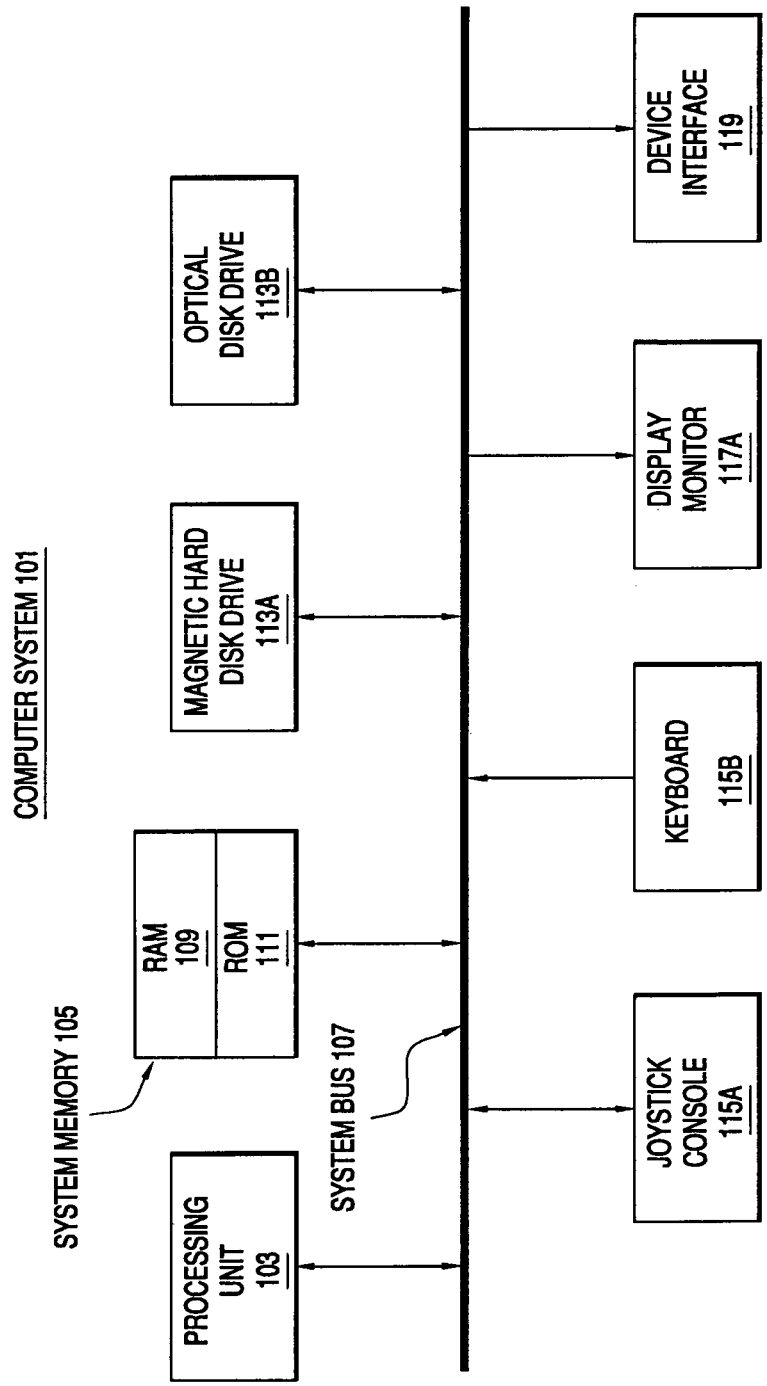
FIG. 1 schematically illustrates an example of a computer that can be used to implement a video game according to various embodiments of the invention.

As will be discussed in more detail below, various embodiments of the invention may employ a video game that offers supplemental functionality corresponding to an amount of physical activity recorded by a footwear-mounted game pod. With some implementations of the invention, one or more aspects of the video game may be implemented using electronic hardware. More typically, however, the various features of a video game according to embodiments of the invention will be implemented by executing software instructions on a programmable computing device or computer. FIG. 1 shows one example of a computer 101 that can be used to implement a video game according to the invention.

The computer system 101 illustrated in FIG. 1 includes a processing unit 103, a system memory 105, and a system bus 107 that couples various system components, including the system memory 105, to the processing unit 103. The system memory 105 may include a read-only memory (ROM) 109 and a random access memory (RAM) 111.

The computer 101 may also include one or more memory storage devices 113, input devices 115, and output devices 117. Thus, as shown in FIG. 1, the computer 101 may include a magnetic hard disk drive 113A, an optical disk drive 113B or both. The input devices 115 employed by the computer 101 may then vary depending upon the intended use of the computer 101. For example, if the computer 101 is intended primarily to host and execute video game software, then the computer 101 may have a joystick console 115A or similar human interface control suitable for gaming. If, however, the computer 101 is intended to operate as a general purpose personal computer (e.g., a conventional desktop or laptop computer), then it may alternately or additionally have a keyboard 115B.

Similarly, the output devices 117 employed by the computer 101 may also vary depending upon the intended use of the computer 101. Typically, most variations of the computer 101 will have a display monitor 117A. If the computer 101 is intended primarily to host and execute video game software, then it also may have speakers. If the computer 101 is configured to operate as a general purpose personal computer, then it may alternately or additionally have a printer. Still other memory storage devices 113, input devices 115 and output devices 117 may include "punch" type memory (where physical indentations are made in the memory medium), holographic memory devices, pressure detectors, cameras, scanners, microphones, and vibrational or other motive feedback devices.

As shown in FIG. 1, the computer 101 additionally has a device interface 119. This device interface 119 may be any type of interface used to obtain data from another device. For example, the device interface 119 may be a conventional connector/port type interface, such as universal serial bus (USB) interface, a Firewire/IEEE 1394 interface, a PS/2 interface, a PC/AT interface, an RS-232 interface, a serial port interface, or an Ethernet port or other telephone-type interface. As will be appreciated by those of ordinary skill in the art, some connector/port type interfaces may have a variety of different configurations. For example, a USB interface may be a USB 1.1 interface or a USB 2.0 interface. It also may be a standard USB interface, a mini USB interface, or a micro USB interface. Accordingly, the device interface 119 may be any type of connector/port type interface of any desired configuration.

The device interface 119 may also be a contact type interface. For example, the device interface 119 may be made up of contacts for establishing an electrical connection with the electrical contacts provided on a flash memory device. Thus, the device interface 119 may have contacts corresponding to the contacts provided on a Sony MEMORY STICK® memory card, a Compact Flash (CF) memory card, a Multi-Media Card (MMC) memory card, a Secure Digital (SD) memory card, a Smart Memory (SM) memory card, an xD memory card, a Personal Computer Memory Card International Association (PCMCIA) port interface or similar device.

Still further, the device interface 119 may include a wireless transceiver for wireless communication with a device. For example, the device interface 119 may be implemented with a radio frequency transceiver, such as a WiFi or Bluetooth wireless transceiver. The device interface 119 may alternately be implemented with an infrared frequency transceiver, a light frequency transceiver, or an ultrasonic frequency transceiver.

If the computer 101 is intended to access other computing devices, it may be capable of operating in a networked environment using logical connections to one or more remote devices, such as other computers. The computer 101 may be connectable to one or more remote devices through a local area network (LAN) or a wide area network (WAN), including the Internet. When used in a networking environment, the computer system 101 may be connected to the network through a network interface, such as a wireless or wired network interface card (NIC) or similar device. The network interface may be an internal interface, or it may alternately be an external network interface as is well known in the art. Of course, it will be appreciated that other means of establishing a communications link with other computers may be used.

The Game Pod

Figure 2:
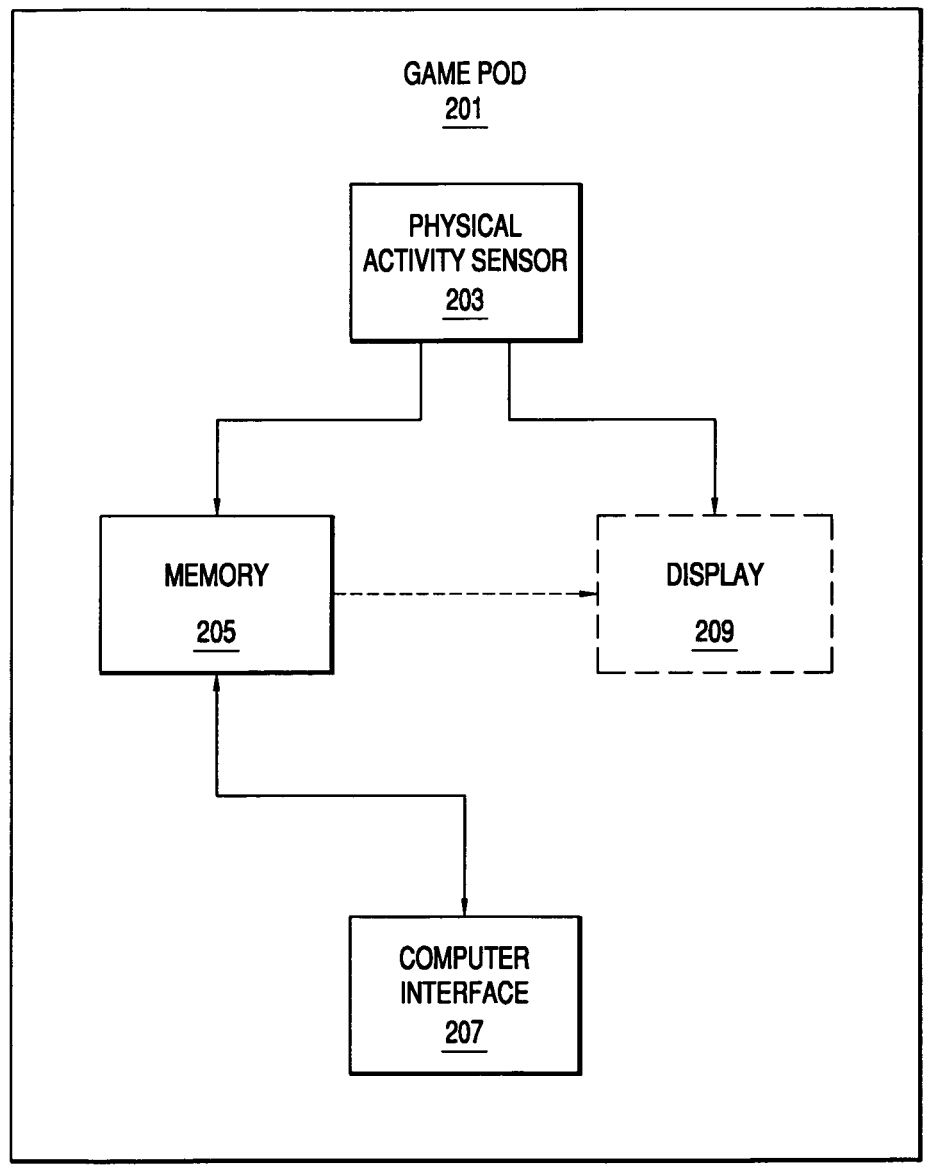
FIG. 2 schematically illustrates an example of a physical activity monitor or game pod according to various embodiments of the invention.

FIG. 2 schematically illustrates an example of a physical activity monitor or "game pod" according to various embodiments of the invention. As seen in this figure, the game pod 201 includes a physical activity detector 203, a memory 205, and a computer interface 207. With various embodiments of the invention, the game pod 201 may additionally include an optional display 209. As noted above, the physical activity detector 203 measures the amount of physical activity performed by a user. This measured amount of physical activity is then recorded in the memory 205. When a user wishes to obtain some advantage or service from a computer, the user then connects the memory 205 to the computer through one of the computer interfaces 207. In this manner, the computer can determine the amount of physical activity recorded in the memory 205.

The physical activity detector 203 may be any type of conventional detector employed to measure an amount of physical activity performed by a user. For example, the physical activity detector 203 may be an accelerometer configured to measure acceleration of a user's foot. With other embodiments of the invention, the physical activity detector 203 may alternately be a pedometer or other type of simple motion-sensing device, such as a contact switch that moves with the user to periodically form and break an electronic circuit in correspondence with a user's motion. As will be discussed in further detail below, still other embodiments of the invention may employ a pressure switch to, for example, accurately record each footstep taken by a user.

With some embodiments of the invention, the physical activity detector 203 may be implemented using a radio frequency position triangulation system, such as the NAVSTAR or Glosnass Global Positioning Satellite (GPS) radio navigation system and the Long Range Navigation (LORAN) radio navigation system, or the satellite positioning system. As known in the art, these positioning systems can be used to periodically determine the change in a user's position, and thus a distance traveled by a user. In addition to detectors that measure distance traveled by a user, various physical activity detectors 203 according to some embodiments of the invention may measure other aspects relating to the amount of physical activity performed by a user. For example, the physical activity detector 203 may be a heart rate monitor or a blood oxygen content monitor. Of course, those of ordinary skill in the art will understand that still other well-known physical activity monitors may be employed with alternate embodiments of the invention.

As previously noted, the amount of physical activity measured by the physical activity detector 203 is stored in the memory 205. With various embodiments of the invention, the memory 205 may be a rewriteable memory (i.e., RAM) implemented by a semiconductor device. Commonly employed conventional memories of this type are often referred to as nonvolatile memories. Of course, with different embodiments of the invention, other types of memories may alternately be employed. For example, some embodiments of the invention may employ a punch memory or even an optical or magnetic disc drive type memory. According to some embodiments of the invention, the memory 205 will continuously record the amount of physical activity measured by the physical activity detector 203 until the memory 205 is reset, as will be discussed in more detail below. In this manner, the memory 205 can record the total cumulative amount of physical activity measured by the physical activity detector 203 between reset operations.

The computer interface 207 likewise may be implemented using any type of conventional interface commonly employed with conventional computer systems. Thus, the computer interface 207 may be any type of interface used to provide data to a computer. For example, the computer interface 207 may be a conventional connector/port type interface, such as universal serial bus (USB) interface, a Firewire/IEEE 1394 interface, a PS/2 interface, a PC/AT interface, an RS-232 interface, a serial port interface, or an Ethernet port or other telephone-type interface. As will be appreciated by those of ordinary skill in the art, some connector/port type interfaces may have a variety of different configurations. For example, a USB interface may be a USB 1.1 interface or a USB 2.0 interface. It also may be a standard USB interface, a mini USB interface, or a micro USB interface. Accordingly, the computer interface 207 may be any type of connector/port type interface of any desired configuration.

The computer interface 207 may also be a contact type interface. For example, the computer interface 207 may be made up of contacts provided on a flash memory device. Thus, the computer interface 207 may be implemented by contacts provided on a Sony MEMORY STICK® memory card, a Compact Flash (CF) memory card, a MultiMedia Card (MMC) memory card, a Secure Digital (SD) memory card, a Smart Memory (SM) memory card, an xD memory card, a Personal Computer Memory Card International Association (PCMCIA) port interface or similar device, while the memory 205 is implemented by the flash memory associated with any one of these cards. This arrangement conveniently allows the memory 205 and computer interface 207 to be removed from the remainder of the game pod 201 as a single unit.

Still further, the computer interface 207 may include a wireless transceiver for wireless communication with a device. For example, the computer interface 207 may be implemented with a radio frequency transceiver, such as a WiFi or Bluetooth wireless transceiver. The computer interface 207 may alternately be implemented with an infrared frequency transceiver, a light frequency transceiver, or an ultrasonic frequency transceiver.

As noted above, various embodiments of the game pod 201 may optionally include a display 209. The display 209 may be any type of conventional display. For example, the display 209 may employ a full color, high resolution, plasma or liquid crystal display screen, a low resolution, monochromatic liquid crystal display screen, or a screen having intermediate performance characteristics and properties. With some embodiments of the invention, the display 209 even may be implemented using a series of lights, such as light emitting diodes.

With some embodiments of the game pod 201, the display 209 can be configured to provide a user with an indication of the amount of measured physical activity stored in the memory 205. The type of indication provided, however, may vary depending upon the display 209. For example, a display 209 with a high-resolution screen may indicate the measured physical activity stored in the memory 205 using text or detailed graphics. A display 209 having a low resolution screen may indicate the measured physical activity stored in the memory 205 using a bar graph or other simple graphics. If the display 209 is implemented using a plurality of lights, then the display 209 may indicate the measured physical activity stored in the memory 205 by sequentially activating a number of the lights corresponding to the measured physical activity. It also should be noted that, rather than simply indicating the measured physical activity stored in the memory 205, various embodiments of the game pod 201 may alternately or additionally use the display 209 to render other data, such as graphics provided by a video game or other software, animation, still or video images, and the like.

Further, while FIG. 2 illustrates only a single computer interface 207, alternate embodiments of the game pod 201 may have two or more different computer interfaces 207. Thus, a game pod 201 may have a first computer interface 207 implemented with a standard USB connector, and another computer interface 207 implemented with a mini USB connector. Having different types of computer interfaces 207 may conveniently allow a user to connect the memory 205 to a computer 201 through a variety of device interfaces 117. For example, a user can connect the memory 205 to one computer 101 that has only a standard USB connector as a device interface 117, but still connect the memory 205 to another computer 101 that has only a mini USB connector as a device interface 117.

Multiple computer interfaces 207 may be particularly useful where the game pod 201 may be employed with both large computers having relatively large device interfaces 117, such as desktop computers and stand-alone video game consoles, and with small computers having relatively small device interfaces 117, such as smart telephones and portable video game consoles. In addition to multiple computer interfaces 207, various embodiments of the game pod 201 may have only a single computer interface 207 that couples to a computer interface adapter. The computer interface adapter may then provide one or more additional computer interfaces, thereby allowing the game pod 201 to connect to a variety of different device interfaces 117.

Similarly, game pods 201 according to various embodiments of the invention may include more than one physical activity detector 203. With some of these embodiments, one or more supplemental physical activity detectors 203 can be used to improve or confirm the accuracy of a primary physical activity detector 203. For example, a game pod 203 may employ both an accelerometer and a pressure detector. The data produced by the pressure detector may then used to improve or confirm the accuracy of the data produced by the accelerometer.

With other embodiments, however, the data measured by two or more physical activity detectors 203 can be separately recorded. The separately recorded data may then be used to, for example, activate different functions in a video game. Alternately, a combination of specific values for different types of recorded physical activity data can be used to activate a particular function of a video game. For example, a video game may require that a player's game pod have recorded both a heart rate over a specified value for a predetermined amount of time and a total traveled distance in excess of another specified value in order to access a particular function of the game.

Game Pod Configuration

Figure 3A:
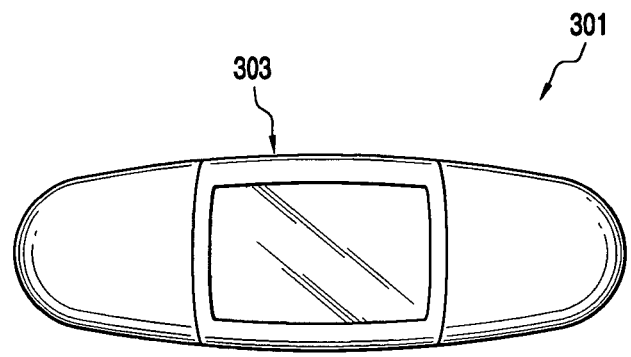
FIGS. 3A and 3B illustrate an example of a container or capsule for a game pod according to various embodiments of the invention.
Figure 3B:
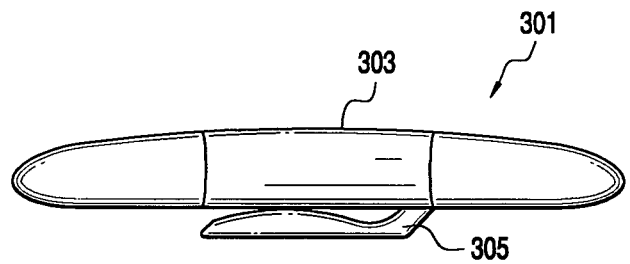

FIGS. 3A and 3B illustrate an example of a container or capsule 301 for a game pod 201 according to various embodiments of the invention. As seen in these figures, the capsule 301 includes a single body 303. The body 303 may be of any desired shape or configuration. As shown in FIGS. 3A and 3B, for example, the body 303 may have an oval shape with a relatively flat thickness. The capsule 301 may also provide a footwear mount that allows the capsule 301 to be mounted to an article of footwear. In the illustrated embodiment, the footwear mount is implemented by a clip 305. The clip 305 and the flat oval shape of the body 303 allow the capsule 301 to conveniently be removably clipped, for example, into the laces of a shoe. This configuration advantageously allows the game pod 201 to be placed where the physical activity monitor can most accurately measure the movement of the user's foot.

Advantageously, removably mounting the game pod 201 to an article of the user's footwear allows the use to unobtrusively carry the game pod 201 throughout almost any athletic activity, including running, walking, hiking, bicycling, skateboarding, and the like. Moreover, by mounting the game pod 201 to an article of footwear, the user need not wear other articles of clothing having pockets, snaps, epaulets, or the like, freeing the user to wear clothing as light as the user's desires during the physical activity.

Figure 4:
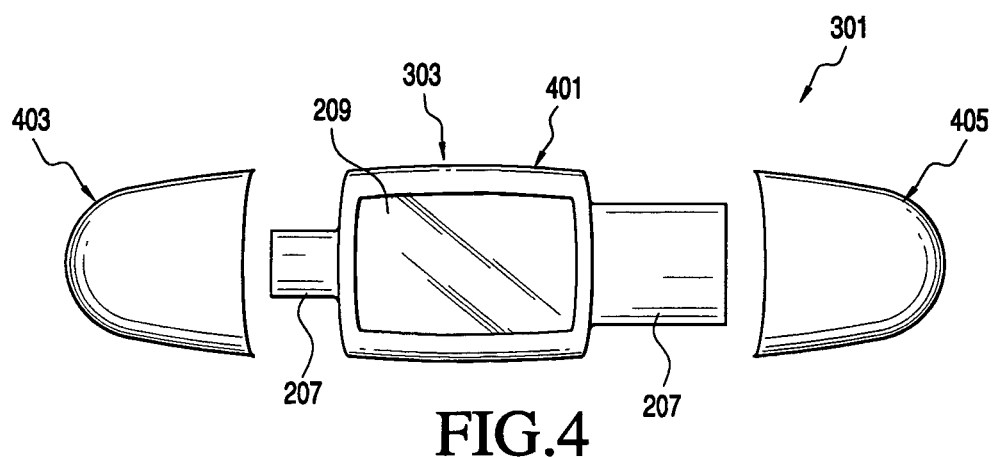
FIG. 4 illustrates an example of a container or capsule for a game pod according to various embodiments of the invention.

It should be appreciated, that with various embodiments of the invention, the capsule 301 may have a plurality of different portions. Thus, as shown in FIG. 4 the body 303 of the capsule 301 may have a main body portion 401, a first end cap 403, and a second end cap 405. As illustrated in this figure, the main body portion 401 of the capsule 301 houses the physical activity detector 203, the memory 205, and two computer interfaces 207. In the illustrated example, one of the computer interfaces 207 is a mini-USB plug while the second interface 207 is a standard USB plug. This configuration conveniently allows the game pod 201 to be connected to a computer if either a USB socket or a mini-USB socket is available. Also, as shown in FIG. 4, if the game pod 201 includes a display 209, then it may be housed in the main portion 401 of the capsule 301.

The first end cap 403 of the capsule 301 then fits over the first computer interface 207, to protect the first interface 207 from dust, debris, and other damaging elements. Similarly, the second end portion 405 of the capsule 301 fits over the second computer interface 207 to protect the second computer interface 207 from dust, debris, and other damage. It should be appreciated that there are still other variations on this type of capsule 401. For example, if the game pod 201 includes only a single computer interface 207, other implementations of the game pod 201 may employ a capsule 401 with only one end portion for covering the single computer interface 207. If, on the other hand, the computer interface 207 is a wireless transceiver integrated with the other components of the game pod 201, then the capsule 401 may be single integrated body.

Figure 5A:
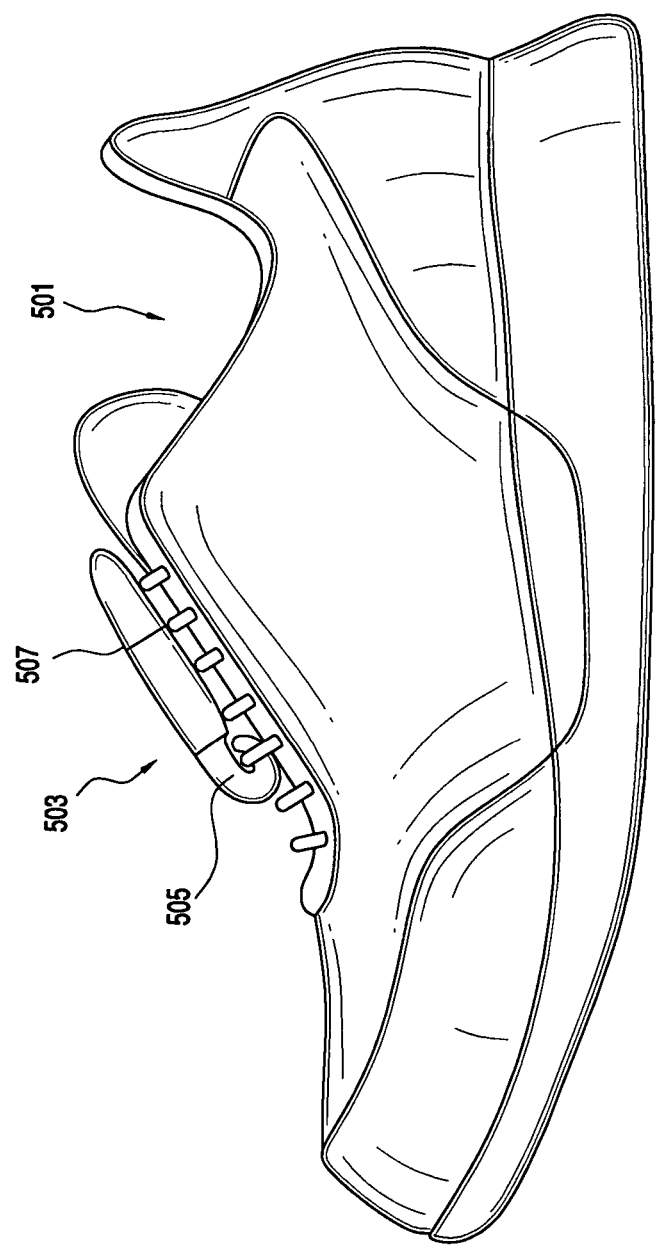
FIGS. 5A and 5B illustrate yet another embodiment of the game pod 201 according to various embodiments of the invention.
Figure 5B:
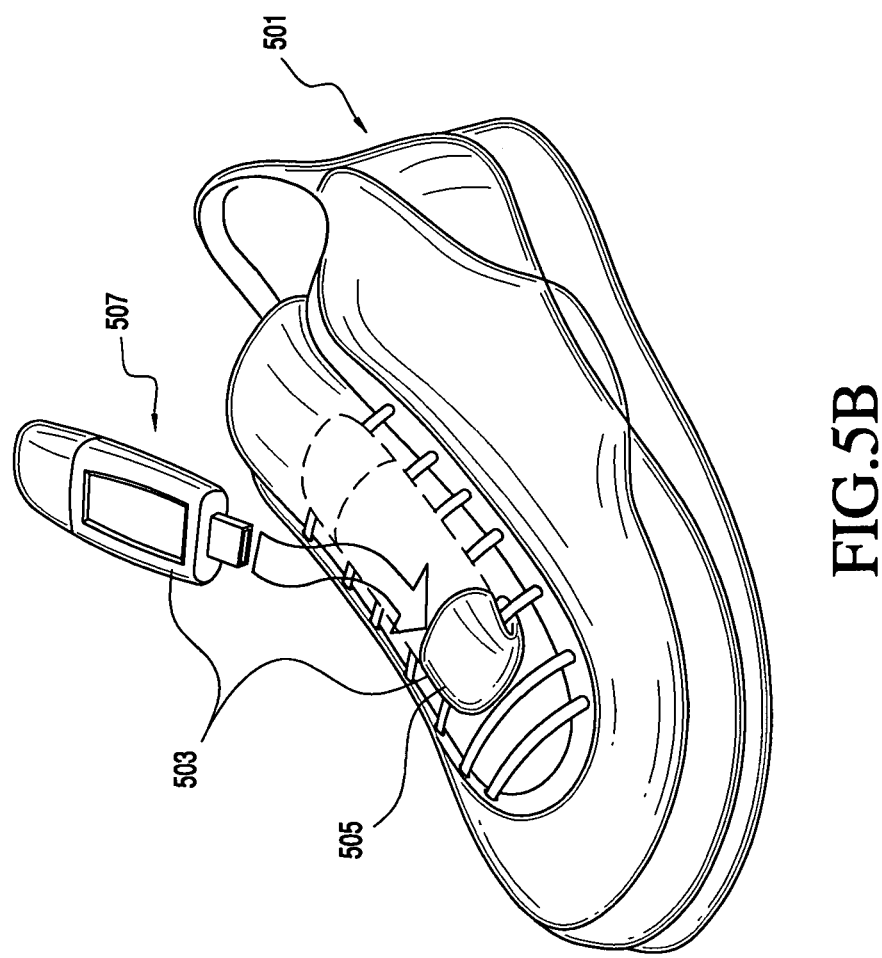

FIGS. 5A and 5B illustrate yet another embodiment of the game pod 201 according to various embodiments of the invention. As seen in these figures, the game pod 201 is integrally formed with or otherwise incorporated into a shoe 501. More particularly, the game pod 201 is contained in a capsule 503. The capsule 503 has a first portion 505 and a second portion 507. The first portion 505 is integrated into the shoe 501 as illustrated in FIGS. 5A and 5B. The second portion of the capsule is then severable from the first portion of the capsule, as shown in FIG. 5B.

With this type of implementation, the physical activity detector 203 may be contained within the first portion of the capsule 505. This conveniently prevents the physical activity detector 203 from being inadvertently separated from the shoe 501. With still other implementations of this type of configuration, the physical activity monitor may be incorporated into the shoe itself. For example, if the physical activity detector 203 is a pressure switch, then the monitor may be located in the sole of the shoe 501. The first portion of the capsule 505 will then include a device interface connected to the physical activity detector 203.

For example, the first portion 505 may include a physical device interface that will connect to a computer interface 207 employed by the game pod 201. Alternately, the first portion 505 may include a wireless device interface, such as a radio frequency transceiver, to communicate with a corresponding computer interface 207 employed by the game pod 201. Still further, the first portion 505 of the capsule 503 may have a physical or wireless interface that communicates with a special purpose corresponding interface in the game pod 201.

The second portion 507 of the capsule 503 then contains the memory 205 and the computer interface or interfaces 207. In the illustrated embodiment, the second portion 507 also includes the display 209. It should be noted, however, that the display 209 alternately may be provided in the first portion 505 of the capsule 503 integrated with the shoe 501.

In still other embodiments of the invention, the physical activity detector 203, the memory 205, and the computer interface or interfaces 207 may all be contained in a removable portion of the capsule 503. With these embodiments, the removable portion may then include an activation mechanism that allows the game pod 201 to work when the first portion 505 of the capsule 503 is connected to the second portion 507, but which prevents the game pod 201 from properly operating when the first portion 505 of the capsule 503 is disconnected from the second portion 507. For example, the activation mechanism may be a physical pin that interacts with a structure in the second portion 507 of the capsule 503 to allow the physical activity detector 203 and/or the memory 205 to operate. Alternately, the activation mechanism may be a microchip or similar device that provides an electronic signal which allows the physical activity detector 203 and/or the memory 205 to operate.

Game Pod/Computer System

Figure 6:
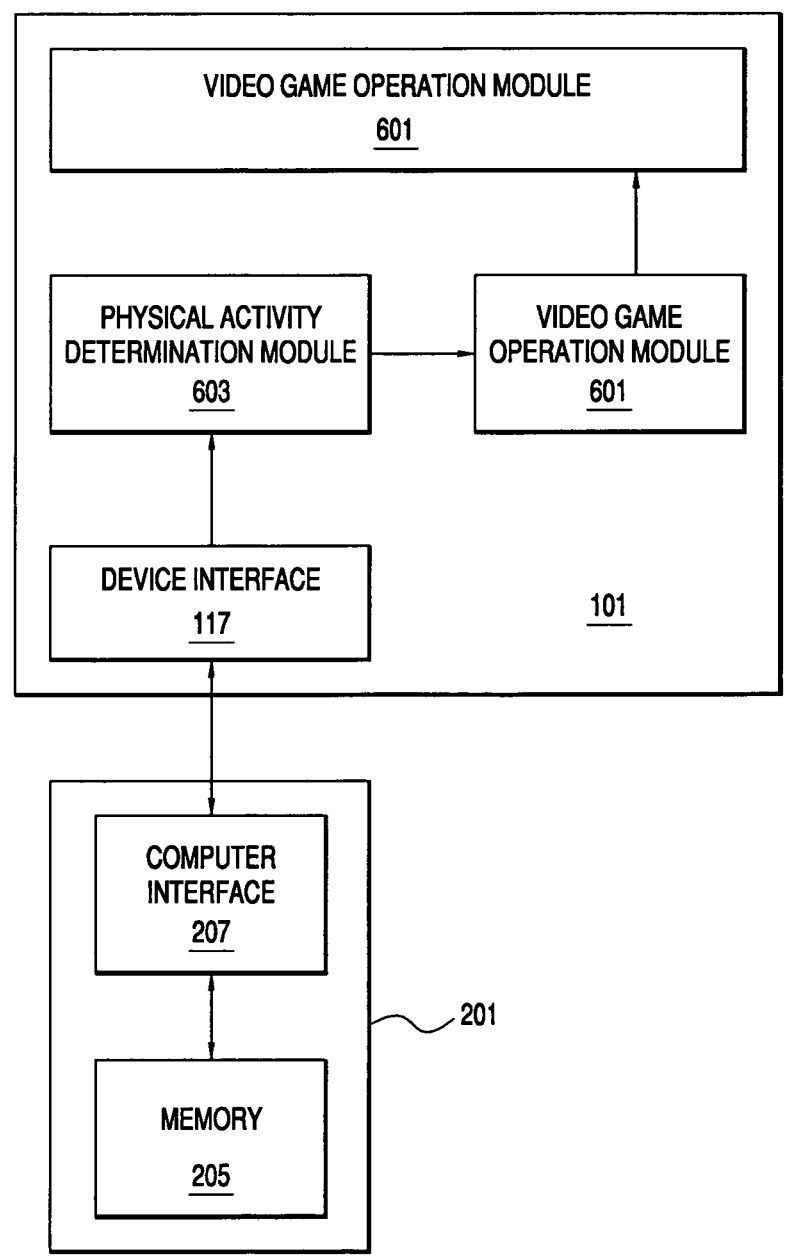
FIG. 6 illustrates an example of a computer according to various embodiments of the invention being employed in conjunction with a game pod according to various embodiments of the invention.
Figure 7A:
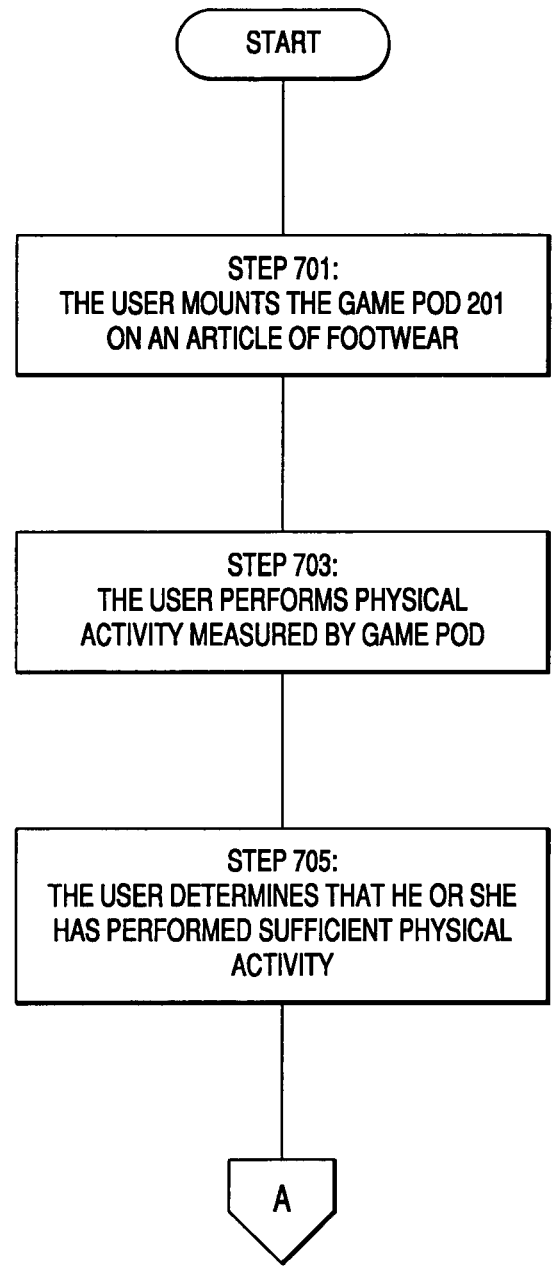
FIGS. 7A-7D illustrate a flowchart describing a method of employing the computer/game pod system shown in FIG. 6.
Figure 7B:
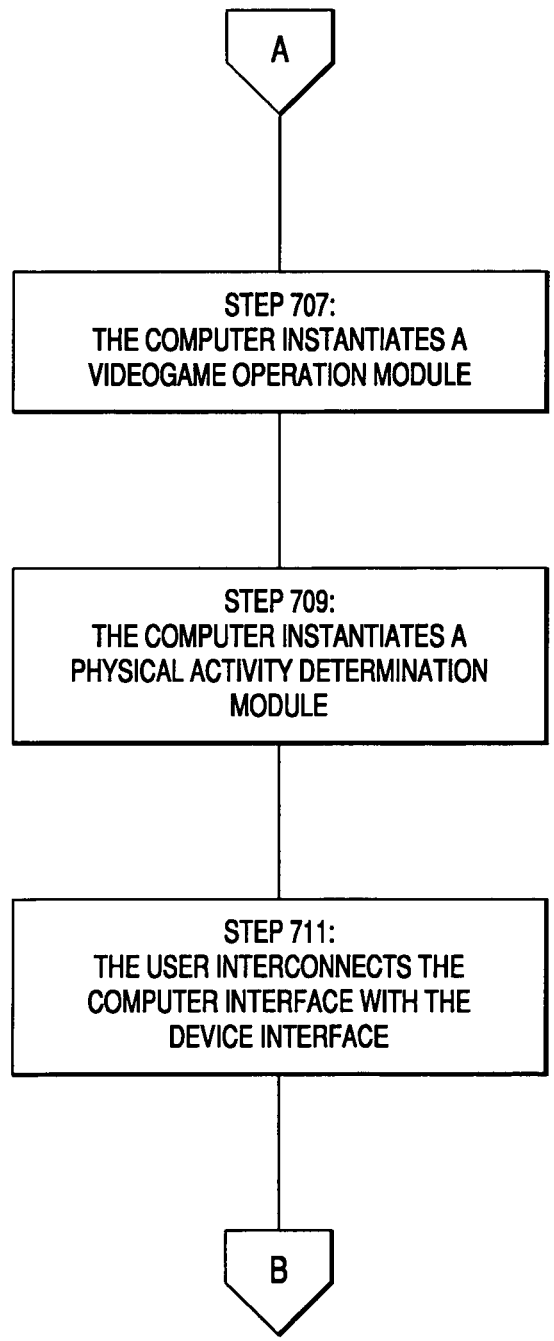
Figure 7C:
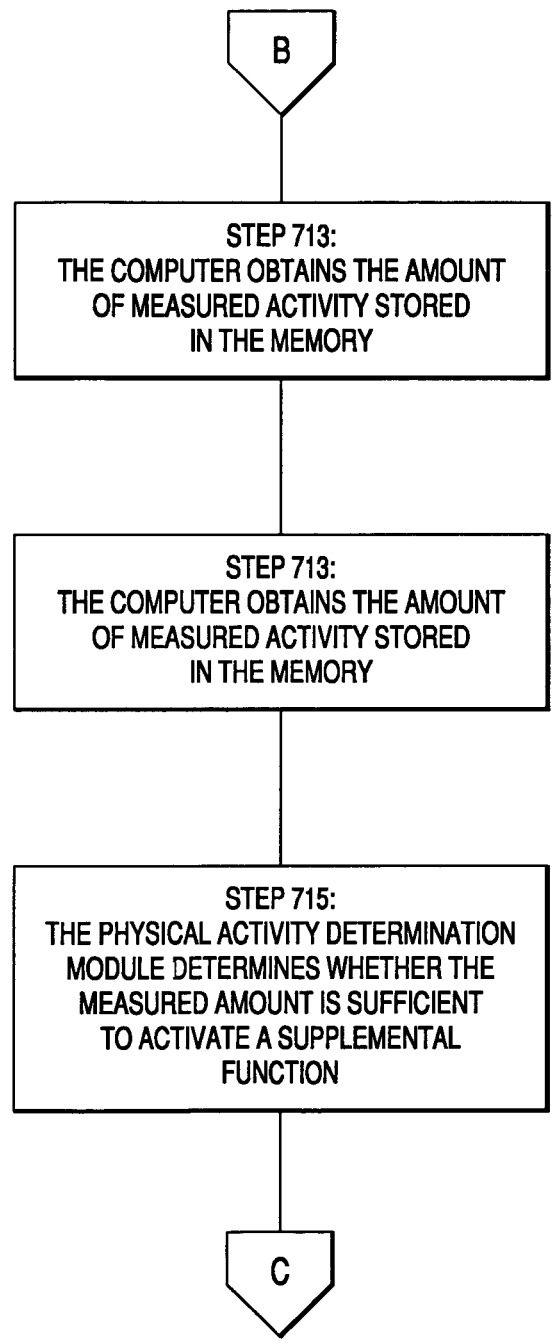
Figure 7D:
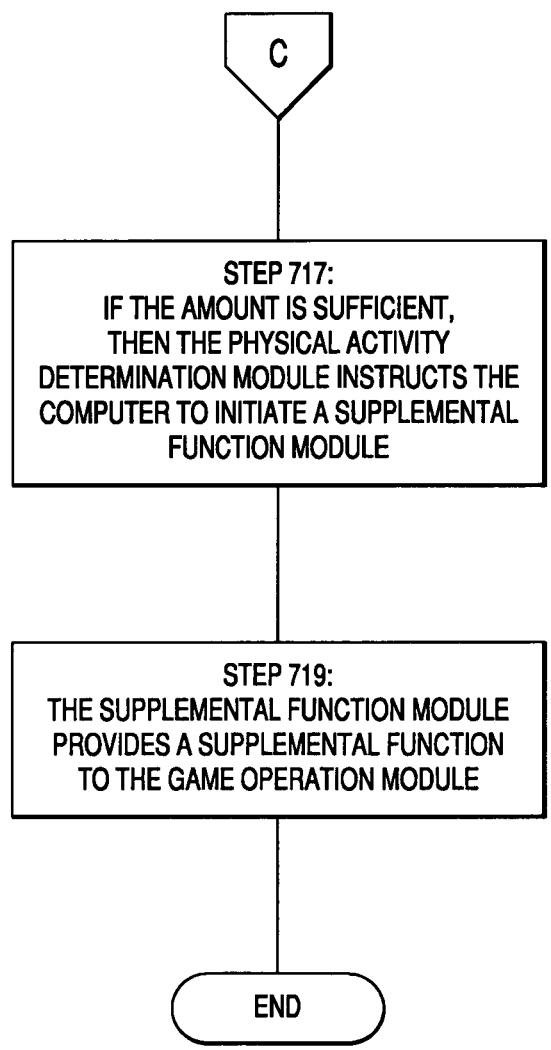

FIG. 6 illustrates an example of a computer 101 according to various embodiments of the invention being employed in conjunction with a game pod 201 according to various embodiments of the invention. The operation of the game pod 201 and the computer 101 will be described in conjunction with the flowchart illustrated in FIG. 7. Initially, in step 701, the user mounts the game pod 201 on an article of footwear and, if necessary, activates the game pod 201. Then, in step 703, the user performs some type of physical activity, which is measured by the physical activity monitor 203 of the game pod 201. Next, in step 705, the user determines that he or she has performed sufficient physical activity to employ a supplemental function associated with an amount of physical activity measured by the game pod 201. With various embodiments of the invention, the amount of physical activity measured by the game pod 201 may be shown on the display. Thus, the user may refer to information shown on the display to determine if the user has accumulated a sufficient measured amount of physical activity to engage a supplemental function for the videogame.

In step 707, the computer 101 executes software code to instantiate a videogame operation module 601 illustrated in FIG. 6. Similarly, in step 709, the computer 101 instantiates a physical activity determination module 603. In step 711, the user interconnects the computer interface 207 of the game pod 201 with the device interface 117 of the computer 101.

Next, in step 713, the computer 101 obtains the amount of measured activity stored in the memory 205 of the game pod 201. With some embodiments of the invention, the computer 201 may automatically obtain the amount of measured activity stored in the memory 205 of the game pod 201. With still other embodiments of the invention, however, a user may be required to activate a button or other trigger to transfer the amount of measured activity stored in the memory 205 to the computer 101. Typically, the memory 205 is cleared when the amount of measured activity stored in the memory 205 is transferred to the computer 101.

Upon receiving the amount of measured activity, the physical activity determination module 603 determines whether the measured amount is sufficient to activate a supplemental function in step 715. If the amount is sufficient to activate the supplemental function, then in step 717 the physical activity determination module 603 instructs the computer to initiate a supplemental function module 605. The supplemental function module 605 then provides a supplemental function to the game operation module 601 in step 719.

With some embodiments of the invention, the game may have different supplemental functions associated with different levels of measured athletic performance. Accordingly, with some embodiments of the invention, the module may instruct the computer to instantiate one or more among a plurality of different supplemental function modules. Alternately, a single function module may be responsible for providing two or more supplemental functions to the videogame operation module. With these implementations, either the module or the supplemental function module may determine which supplemental functions will be provided by the supplemental function module based upon the measured amount of physical activity.

The supplemental functions may be any function desired with a video game. For example, a supplemental function may include the instantiation of a specified gaming environment within a video game. Thus, a user that has performed a specified amount of a physical activity may have access to gaming environments that are otherwise unavailable. A supplemental function also may include the instantiation of one or more specified characteristics for a user's avatar within a video game. For example, a user's avatar may gain virtual strength, endurance or speed characteristics based upon the amount of physical activity performed by the user. Still further, the supplemental function may permit the user to access particular data associated with the video game. With some embodiments of the invention, a supplemental function may even include the valid operation of the video game itself. With this arrangement, a user may not be able to play the video game until after the user has performed a specified amount of a physical activity. This feature may be particularly useful where a parent wishes to restrict a child from playing a video game until after the child has performed a desired amount of physical exercise.

CONCLUSION

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A system comprising:
    a physical activity monitor comprising:
        a detector configured to measure an amount of physical exercise performed by a user;
        a storage device configured to store the amount of physical exercise;
        an interface configured to transfer the amount of physical exercise;
        a mount configured for attaching the detector to the user; and
    a computer hosting a video game and comprising:
        a processor; and
        a memory storing instructions that, when executed, cause the apparatus to at least:
            (a) receive an amount of physical exercise from the storage device via the interface;
            (b) determining whether the amount of physical exercise is sufficient to activate a supplemental function of the computer hosting the video game;
        wherein the supplemental function permits access to a specified gaming environment within the video game.

2. The system of claim 1, wherein the supplemental function includes the instantiation of one or more specified characteristics for a user's avatar within the video game.

3. The system of claim 1, wherein (b) comprises determining whether the amount of physical exercise exceeds a physical performance metric for a predetermined amount of time.

4. The system of claim 1, wherein (b) comprises determining whether the amount of physical exercise exceeds a distance traveled value.

* * * * *